United States Patent [19]

Leyendecker et al.

[11] Patent Number: 4,929,617

[45] Date of Patent: May 29, 1990

[54] 2-TERT-BUTYL-5-ISOXAZOLYLMETHYLTHIO-3(2H)-PYRIDAZIN-3-ONE

[75] Inventors: Joachim Leyendecker, Mannheim; Rainer Buerstinghaus, Telgte; Hans Theobald, Limburgerhof; Christoph Kuenast, Otterstadt; Peter Hofmeister, Neustadt, all of Fed. Rep. of Germany

[73] Assignee: BASF Aktiengesellschaft, Ludwigshafen, Fed. Rep. of Germany

[21] Appl. No.: 283,128

[22] Filed: Dec. 12, 1988

[30] Foreign Application Priority Data

Dec. 12, 1987 [DE] Fed. Rep. of Germany ....... 3742266

[51] Int. Cl.$^5$ ..................... A31K 31/50; C07D 231/04
[52] U.S. Cl. .................... 514/252; 544/238; 544/239
[58] Field of Search ........................ 544/238; 514/252; 548/247

[56] References Cited

U.S. PATENT DOCUMENTS 4,268,678 5/1981 Diana et al. ................... 548/247
4,411,753 10/1983 Abdulla .......................... 544/239
4,451,476 5/1984 Diana ............................. 548/247
4,837,217 6/1989 Ogura et al. .................... 544/238

FOREIGN PATENT DOCUMENTS 0199281 10/1986 European Pat. Off. .

Primary Examiner—Donald G. Daus
Attorney, Agent, or Firm—Oblon, Spivak, McClelland, Maier & Neustadt

[57] ABSTRACT

2-tert-butyl-5-isoxazolylmethylthio-3(2H)-pyridazin-3-one derivatives of the general formula t,10 where $R^1$ is hydrogen or $C_1$–$C_4$-alkyl, $R^2$ is hydrogen, $C_1$–$C_8$-alkyl, $C_2$–$C_8$-alkenyl, $C_1$–$C_4$-haloalkenyl, $C_2$–$C_8$-alkoxyalkyl, $C_3$–$C_{10}$-cycloalkyl, $C_2$–$C_5$-alkoxycarbonyl, aryl or $C_7$–$C_{20}$-aralkyl, or aryl which is monosubstituted, disubstituted or trisubstituted by halogen, $C_1$–$C_8$-alkyl, $C_1$–$C_8$-alkoxy, $C_1$–$C_4$-haloalkyl, $C_1$–$C_4$-haloalkoxy, phenyl, phenoxy or cyano and/or monosubstituted or disubstituted by nitro or $C_7$–$C_{20}$-aralkyl substituted by the said substituents in the aryl moiety, $R^3$ is hydrogen, halogen, $C_1$–$C_8$-alkyl or $C_2$–$C_8$-alkenyl and X is chlorine or bromine, their preparation and their use for controlling pests.

5 Claims, No Drawings

2-TERT-BUTYL-5-ISOXAZOLYLMETHYLTHIO-3(2H)-PYRIDAZIN-3-ONE

The present invention relates to novel 2-tertbutyl-5-isoxazolylmethylthio-3(2H)-pyridazin-3-one derivatives of the general formula I

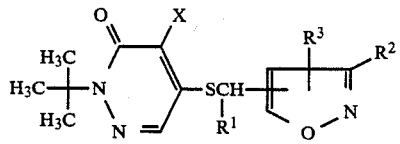

where $R^1$ is hydrogen or $C_1$–$C_4$-alkyl, $R^2$ is hydrogen, $C_1$–$C_8$-alkyl, $C_2$–$C_8$-alkenyl, $C_1$–$C_4$-haloalkenyl, $C_2$–$C_8$-alkoxyalkyl, $C_3$–$C_{10}$-cycloalkyl, $C_2$–$C_5$-alkoxycarbonyl, aryl or $C_7$–$C_{20}$-aralkyl, or aryl which is monosubstituted, disubstituted or trisubstituted by halogen, $C_1$–$C_8$-alkyl, $C_1$–$C_8$-alkoxy, $C_1$–$C_4$-haloalkyl, $C_1$–$C_4$-haloalkoxy, phenyl, phenoxy or cyano and/or monosubstituted or disubstituted by nitro or $C_7$–$C_{20}$-aralkyl which is substituted by the said substituents in the aryl moiety, $R^3$ is hydrogen, halogen, $C_1$–$C_8$-alkyl or $C_2$–$C_8$-alkenyl and X is chlorine or bromine.

The present invention furthermore relates to the preparation of the compounds I, pesticides which contain the compounds I as active ingredients and a method for controlling pests.

EP-A-199 281 discloses a large number of 3(2H)-pyridazinone derivatives which are substituted by hetaryl radicals but whose insecticidal and acaricidal action is unsatisfactory. The compounds described there do not contain an isoxazolyl radical as the hetaryl radical.

It is an object of the present invention to provide novel 3(2H)-pyrizadinone derivatives which are substituted by heterocyclic radicals and have an improved action.

We have found that this object is achieved by the novel 2-tert-butyl-5-isoxazolylmethylthio-3(2H)-pyridazin-3-one derivatives defined at the outset of the general formula I and processes for their preparation. We have also found that the compounds I are very well tolerated by plants and are suitable for controlling pests.

The substituents in formula I have the following specific meanings:

$R^1$ is hydrogen or
straight-chain or branched $C_1$–$C_4$-alkyl, preferably $C_1$- or $C_2$-alkyl, particularly preferably methyl,
$R^2$ is hydrogen,
straight-chain or branched $C_1$–$C_8$-alkyl, such as methyl, ethyl, n-propyl, isopropyl, n-butyl, isobutyl, sec-butyl, tert-butyl, n-hexyl, 1-ethylpent-1-yl or 2,4,4-trimethylpent-1-yl, preferably methyl, isoproyl, tert-butyl, 1-ethylpent-1-yl or 2,4,4-trimethylpen-1-yl,
straight-chain or branched $C_2$–$C_8$-alkenyl, preferably $C_2$–$C_5$-alkenyl, such as vinyl, allyl or 2,2-dimethylvinyl, straight-chain or branched $C_1$–$C_4$-haloalkyl, such as 1,2-dibromo-2,2-dimethylethyl, preferably $C_1$- or $C_2$-fluoro-or chloroalkyl, such as fluoromethyl, difluoromethyl, trifluoromethyl, chloromethyl, difloromethyl, trichloromethyl, chlorofluoromethyl, dichlorofluoromethyl, chlorodifluoromethyl, 2,2,2-trifluoroethyl or 2,2,2-trichloroethyl,
straight-chain or branched $C_2$–$C_8$-alkoxyalkyl, preferably $C_2$–$C_4$-alkoxyalkyl, such as methoxymethyl, ethoxymethyl, n-propoxymethyl, isopropoxymethyl, 1-methoxethyl, 2-methoxyethyl, 1-ethoxyethyl, 2-ethoxyethyl, 1-n-propoxyethyl, 2-n-propoxyethyl, 1-isopropoxyethyl, 2-isopropoxyethyl, 1-methoxy-n-propyl, 2-methoxy-n-propyl, 3-methoxy-n-propyl, 1-methoxyisopropyl or 2-methoxyisopropyl, $C_3$–$C_{10}$-cycloalkyl, preferably cyclopropyl, cyclobutyl, cyclopentyl, cyclohexyl, cyclooctyl or cyclodecyl, $C_2$–$C_5$-alkoxycarbonyl, preferably $C_2$- or $C_3$-alkoxycarbonyl, such as methoxycarbonyl or ethoxycarbonyl, aryl, preferably phenyl or naphthyl, particularly preferably phenyl, $C_7$–$C_{20}$-aralkyl, preferably $C_7$–$C_{12}$-phenylalkyl, such as benzyl or phenethyl, aryl which is monosubstituted, disubstituted or trisubstituted by halogen, preferably phenyl which is monosubstituted, disubstituted or trisubstituted by fluorine, chlorine or bromine, such as 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2,3-difluorophenyl, 2,3-dichlorophenyl, 2,4-difluorophenyl, 2,4-dichlorophenyl, 2-chloro-4-fluorophenyl, 4-chloro-2-fluorophenyl, 2,5-difluorophenyl, 2,5-dichlorophenyl, 3,4-difluorophenyl, 3,4-dichlorophenyl, 3,5-difluorophenyl, 3,5-dichlorophenyl, 3-chloro-5-fluorophenyl, 5-chloro-3-fluorophenyl, 2,6-difluorophenyl, 2,6-dichlorophenyl, 2-chloro-6-fluorophenyl, 6-chloro-2-fluorophenyl, 2,3,4-trifluorophenyl, 2,3,4-trichlorophenyl, 2,4,6-trifluorophenyl or 2,4,6-trichlorophenyl, aryl which is monosubstituted, disubstituted or trisubstituted by $C_1$–$C_8$-alkyl, preferably phenyl which is monosubstituted, disubstituted or trisubstituted by $C_1$–$C_4$-alkyl, such as 2-methylphenyl, 3-methylphenyl, 4-methylphenyl, 2-ethylphenyl, 3-ethylphenyl, 4-ethylphenyl, 2-n-propylphenyl, 3-n-propylphenyl, 4-n-propylphenyl, 3-iso-propylphenyl, 4-isopropylphenyl, 2-n-butylphenyl, 3-n-butylphenyl, 4-n-butylphenyl, 3-isobutylphenyl, 4-isobutylphenyl, 3-sec-butylphenyl, 4-sec-butylphenyl, 3-tert-butylphenyl, 4-tert-butylphenyl, 2,3-dimethylphenyl, 2,4-dimethylphenyl, 2,5-dimethylphenyl, 3,4-dimethylphenyl, 3,5-dimethylphenyl, 2,6-dimethylphenyl, 3,6-dimethylphenyl, 2,4-diethylphenyl, 2,4-diisopropylphenyl, 3,5-di-tert-butylphenyl, 2,6-di-tert-butylphenyl, 2,4,6-trimethylphenyl, 2,3,4-trimethylphenyl, 2,3,5-trimethylphenyl or 3,4,5-trimethylphenyl, aryl which is monosubstituted, disubstituted or trisubstituted by $C_1$–$C_8$-alkoxy, preferably phenyl which is substituted by $C_1$–$C_8$-alkoxy, such as 2-mehtoxyphenyl, 3-methoxyphenyl, 4-methoxyphenyl, 2-ethoxyphenyl, 3-ethoxyphenyl, 4-ethoxyphenyl, 2-n-propoxyphenyl, 3-n-propoxyphenyl, 4-n-propoxyphenyl, 3-isopropoxyphenyl, 4-isopropoxyphenyl, 2-n-butoxyphenyl, 3-n-butoxyphenyl, 4-n-butoxyphenyl, 2-sec-butoxyphenyl, 4-sec-butoxyphenyl, 2-tert-butoxyphenyl, 4-tert-butoxyphenyl, 2-n-hexyloxyphenyl, 3-n-hexyloxyphenyl, 4-n-hexyloxyphenyl, 2-n-octyloxyphenyl, 3-n-octyloxyphenyl, 4-n-octyloxyphenyl, 2,3-dimethoxyphenyl, 2,4-dimethoxyphenyl, 3,4-dimethoxyphenyl, 2,5-dimethoxyphenyl, 3,5-dimethoxyphenyl, 2,6-dimethoxyphenyl, 3,4-diethoxyphenyl, 2,3,4-trimethoxyphenyl, 2,3,5-trimethoxyphenyl, 2,4,5-trimethoxyphenyl, 2,4,6-trimethoxyphenyl or 3,4,5-trimethoxyphenyl, aryl which is monosubstituted, disubstituted or trisubstituted by $C_1$–$C_4$-haloalkyl, preferably phenyl which is monosubstituted by $C_1$- or $C_2$-alkyl monosubstituted to pentasubstituted by fluorine and/or chlorine, such as 2-fluoromethylphenyl, 3-fluoromethylphenyl, 4-fluoromethylphenyl, 2-difluoromethylphenyl, 3-difluoromethylphenyl, 4-difluoromethylphenyl, 2-trifluoromethylphenyl, 3-trifluoromethylphenyl, 4-trifluoromethylphenyl, 2-chloromethylphenyl, 3-chloromethylphenyl, 4-chloromethylphenyl, 2-dichloromethylphenyl, 3-dichloromethylphenyl, 4-dichloromethylphenyl, 2-trichloromethylphenyl, 3-trichloromethylphenyl, 4-trichloromethylphenyl, 2-chlorofluoromethylphenyl, 3-chlorofluoromethylphenyl, 4-chlorofluoromethylphenyl, 2-dichlorofluoromethylphenyl, 3-dichlorofluoromethylphenyl, 4-dichlorofluoromethylphenyl, 2-chlorodifluoromethylphenyl, 3-chlorodifluoromethylphenyl, 4-chlorodifluoromethylphenyl, 1,1-difluoroethylphenyl, 1,1,-dichloroethylphenyl, ortho-, meta- or para-1,1,2-trifluoroethylphenyl, ortho-, meta- or para-1,1,2-trichloroethylphenyl, ortho-, meta- or para-1,1,2,2-tetrafluoroethylphenyl, ortho-, meta- or para-1,1,2,2-tetrachloroethylphenyl, ortho-, meta- or para-1,2,2,2-tetrafluoroethylphenyl, ortho-, meta- or para-1,2,2,2-tetrachloroethylphenyl, ortho-, meta- or para-pentafluoroethylphenyl and ortho-, meta- or para-pentachloroethylphenyl, aryl which is monosubstituted, disubstituted or trisubstituted by $C_1$–$C_4$-haloalkoxy, preferably phenyl which is monosubstituted by $C_1$- or $C_2$-alkoxy which is monosubstituted to pentasubstituted by fluorine and/or chlorine, such as 2-fluromethoxyphenyl, 3--fluoromethoxyphenyl, 4-fluoromethoxyphenyl, 2-difluoromethoxyphenyl, 3-difluoromethoxyphenyl, 4-difluoromethoxyphenyl, 2-trifluoromethoxyphenyl, 3-trifluoromethoxyphenyl, 4-trifluoromethoxyphenyl, 2-chloromethoxyphenyl, 3-chloromethoxyphenyl, 4-chloromethoxyphenyl, 2-dichloromethoxyphenyl, 3-dichloromethoxyphenyl, 4-dichloromethoxyphenyl, 2-trichloromethoxyphenyl, 3-trichloromethoxyphenyl, 4-trichloromethoxyphenyl, 2-chlorofluoromethoxyphenyl, 3-chlorofluoromethoxyphenyl, 4-chlorofluoromethoxyphenyl, 2-dichlorofluoromethoxyphenyl, 3-dichlorofluoromethoxyphenyl, 4-dichlorofluoromethoxyphenyl, 2-chlorodifluoromethoxyphenyl, 3-chlorodifluoromethoxyphenyl, 4-chlorodifluoromethoxyphenyl, 1,1-difluoroethoxyphenyl, 1,1-dichloroethoxy-phenyl, ortho-, meta- or para-1,1,2-trifluoroethoxyphenyl, ortho-, meta- or para-1,1,2-trichloroethoxyphenyl, ortho-, meta- or para-1,1,2,2-tetrafluoroethoxyphenyl, ortho-, meta - or para-1,1,2,2-tetrachloroethoxyphenyl, ortho-, meta- or para-1,1,2,2-tetrafluoroethoxyphenyl, ortho-, meta- or para-1,1,2,2-tetrachloroethoxyphenyl, ortho-, meta- or para-pentafluoroethoxyphenyl and ortho-, meta-or para-pentachloroethoxyphenyl, aryl which is monosubstituted, disubstituted or trisubstituted by phenyl, preferably phenyl which is monosubstituted by phenyl, such as 2-phenylphenyl, 3-phenylphenyl and 4-phenylphenyl, aryl which is monosubstituted, disubstituted or trisubstituted by phenoxy, preferably phenyl which is monosubstituted by phenoxy, such as 2-phenoxyphenyl, 3-phenoxyphenyl or 4-phenoxyphenyl, aryl which is monosubstituted, disubstituted or trisubstituted by cyano, preferably phenyl which is monosubstituted by cyano, such as 2-cyanophenyl, 3-cyanophenyl or 4-cyanophenyl, aryl which is monosubstituted or disubstituted by nitro, preferably phenyl which is monosubstituted or disubstituted by nitro, such as 2-nitrophenyl, 3-nitrophenyl, 4-nitrophenyl, 2,3-dinitrophenyl, 2,4-dinitrophenyl, 3,4-dinitrophenyl, 2,5-dinitrophenyl, 3,5-dinitrophenyl or 2,6-dinitrophenyl, aryl which is disubstituted or trisubstituted by halogen and nitro, preferably phenyl which is disubstituted or trisubstituted by fluorine and/or chlorine and nitro, such as 2-fluoro-3-nitrophenyl, 2-fluoro-4-nitrophenyl, 2-fluoro-5-nitrophenyl, 2-fluoro-6-nitrophenyl, 2-chloro-3-nitrophenyl, 2-chloro-4-nitrophenyl, 2-chloro-5-nitrophenyl, 2-chloro-6-nitrophenyl, 3-chloro-2-nitrophenyl, 4-chloro-2-nitrophenyl, 4-chloro-3nitrophenyl, 5-chloro-2-nitrophenyl, 2,4-dichloro-5-nitrophenyl, 2,6-dichloro-5-nitrophenyl, 2,6-dichloro-3-nitrophenyl or 2,4-dichloro-3-nitrophenyl, aryl which is disubstituted or trisubstituted by $C_1$–$C_4$-alkyl and nitro, preferably phenyl which is disubstituted or trisubstituted by $C_1$- or $C_2$-alkyl and nitro, such as 2-methyl-3-nitrophenyl, 4-methyl-3-nitrophenyl or 2,6-dimethyl-3-nitrophenyl, aryl which is disubstituted or trisubstituted by halogen and $C_1$–$C_4$-alkoxy, preferably phenyl which is disubstituted or trisubstituted by bromine and $C_1$- or $C_2$-alkoxy, such as 3-bromo-2-methoxyphenyl, 4-bromo-2-methoxyphenyl, 5-bromo-2-methoxy-phenyl, 2-bromo-4-methoxyphenyl or 3-bromo-4-methoxyphenyl, $C_7$–$C_{20}$-aralkyl which is monosubstituted, disubstituted or trisubstituted in the aryl moiety by halogen, preferably $C_7$–$C_{10}$-phenylalkyl which is monosubstituted in the phenyl moiety by fluorine or chlorine, such as 4-fluorobenzyl or 4-chlorobenzyl, $C_7$–$C_{20}$-aralkyl which is monosubstituted, disubstituted or trisubstituted in the aryl moiety by $C_1$–$C_8$-alkyl, preferably $C_7$–$C_{10}$-phenylalkyl which is monosubstituted in the phenyl moiety by $C_1$–$C_4$-alkyl, particularly preferably $C_7$–$C_{10}$-phenylalkyl which is monosubstituted in the phenyl moiety by $C_1$- or $C_2$-alkyl, such as 4-methylphenyl, 4-ethylbenzyl, 4-methylphenethyl or 2-(4-tert-butylphenyl)-1-methylethyl, $C_7$–$C_{20}$-aralkyl which is monosubstituted, disubstituted or trisubstituted in the aryl moiety by $C_1$–$C_8$-alkoxy, preferably $C_7$–$C_{10}$-phenylalkyl which is monosubstituted in the phenyl moiety by $C_1$–$C_4$-alkoxy, particularly preferably $C_7$–$C_{10}$-phenylakyl which is monosubstituted in the phenyl moiety by $C_1$- $C_2$-alkoxy, such as 4-methoxybenzyl, 4-ethoxybenzyl or 4-methoxyphenethyl, $C_7$–$C_{20}$-aralkyl which is monosubstituted, disubstituted or trisubstituted in the aryl moiety by $C_1$–$C_4$-haloalkyl, preferably $C_7$–$C_{10}$-phenylalkyl which is monosbstituted in th ephenyl moiety by $C_1$–$C_4$-fluoro- or chloroalkyl, particularly preferably $C_7$–$C_{10}$-phenylalkyl which is monosubstituted in the phenyl moiety by $C_1$- or $C_2$-fluoro - or chloroalkyl, such as 4-trifluoromethylbenzyl or 4-trichloromethylbenzyl, $C_7$–$C_{20}$-aralkyl which is monosubstituted, disubstituted or trisubstituted in the aryl moiety by $C_1$–$C_4$-haloalkoxy, preferably $C_7$–$C_{10}$-phenylalkyl which is monosubstituted in the phenyl moiety by $C_1$- or $C_2$-haloalkoxy, particularly preferably $C_7$–$C_{10}$-phenylalkyl which is monosubstituted by trifluoromethoxy or trichloromethoxy, such as 4-trifluoromethoxybenzyl or 4-trichloromethoxybenzyl, $C_7$–$C_{20}$-aralkyl which is monosubstituted, disubstituted or trisubstituted in the aryl moiety by cyano, preferably $C_7$–$C_{10}$-phenylalkyl which is monosubstituted in the phenyl moiety by cyano, such as 4-cyanobenzyl or 4-cyanophenethyl, or C$_7$-C$_{20}$-aralkyl which is monosubstituted or disubstituted in the aryl moiety by nitro, preferably C$_7$-C$_{10}$-phenylalkyl which is monosubstituted by nitro, such as 3-nitrobenzyl, R$^3$ is hydrogen, preferably in the 4-position, halogen, preferably fluorine, chlorine or bromine, particularly preferably bromine in the 5-position, straight-chain or branched C$_1$-C$_8$-alkyl, preferably straight-chain or branched C$_1$-C$_4$-alkyl, particularly preferably methyl in the 5-position, or straight-chain or branched C$_2$-C$_8$-alkenyl, preferably straight-chain or branched C$_2$-C$_4$-alkenyl, particularly preferably vinyl, methylvinyl or dimethylvinyl, and X is chlorine or bromine, preferably chlorine.

The compounds I are obtainable by the following method:

A 2-tert-butyl-5-mercapto-3(2H)-pyridazione of the formula II and an isoxazole of the general formula III are reacted in the presence of a base at from −20° to 250° C., preferably from 20° to 120° C., in accordance with the following equation:

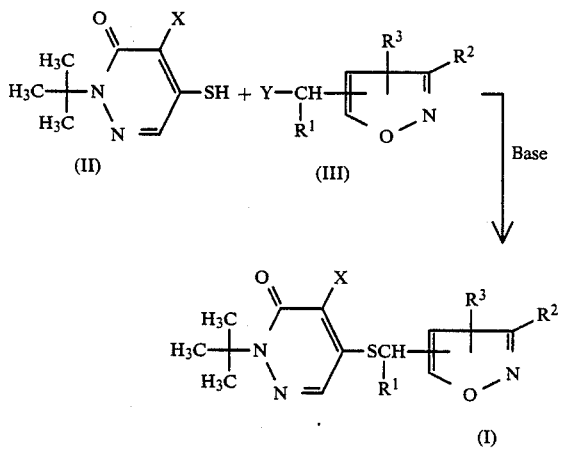

2-tert-butyl-5-mercapto-3(2H)pyridazinones of the formula II are disclosed in EP-A-134 439 and can be prepared by the methods described there.

Some of the isoxazoles of the general formula III are disclosed in DE-A-25 49 962 and DE-A-27 54 832 and can be obtained by the methods, described there.

Y is a leaving group, for example a sulfo radical or halogen. Among the sulfonic esters, methanesulfonyl, trifluoromethanesulfonyl, benzenesulfonyl and p-toluenesulfonyl are preferred, while preferred halogens are chlorine and bromine, chlorine being particularly preferred.

For the preparation of the novel compounds I by the methods described above, the starting materials are usually reacted in a stoichiometric ratio. An excess of one or other of the components may be advantageous.

The reactions usually take place at a sufficiently high rate at above −20° C. In general, there is no need to exceed 120° C. Since they take place with evolution of heat in some cases, it may be advantageous to provide a means of cooling.

Usually, not less than an equivalent amount of a base is added to II and/or III, although the base can also be used in excess or, if required, also as a solvent. Examples of suitable bases are hydroxides of alkali metals and of alkaline earth metals, such as sodium hydroxide, potassium hydroxide and calcium hydroxide, alcoholates of alkali metals and of alkaline earth metals, such as sodium methylate, sodium ethylate, calcium methylate or potassium tert-butylate, alkali metal or alkaline earth metal hydrides, such as sodium hydride, potassium hydride or calcium hydride, alkali metal or alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, and aromatic amines, such as pyridine or pyrrole.

The reaction is advantageously carried out in a solvent or diluent. Examples of suitable solvents or diluents for this purpose are aliphatic hydrocarbons, such as n-pentane, n-hexane, the hexane isomer mixture and petroleum ether, halohydrocarbons, such as chlorobenzene, methylene chloride, ethylene chloride, chloroform or tetrachloroethylene, aromatic hydrocarbons, such as benzene, toluene, the xylenes and their isomer mixtures, gasoline, alcohols, such as methanol, ethanol, n-propanol and isopropanol, ethers, such as diethyl ether, di-n-butyl ether, methyl tert-butyl ether, tetrahydrofuran and dioxane, ketones, such as acetone, methyl ethyl ketone and methyl isopropyl ketone, nitriles, such as acetonitrile and propionitrile, and aprotic dipolar solvents, such as dimethylformamide, dimethyl sufoxide or pyridine. Mixtures of these substances can also be used as solvents and diluents.

Advantageously, the 2-tert-butyl-5-mercapto-3(2H)-pyridazinone of the formula II in a diluent or solvent is initially taken and the isoxazole III is then added. The novel compounds I are isolated by a conventional method. The products obtained can be purified by recrystallization, extractions or chromatography.

The 2-tert-butyl-5-isoxazolylmethylthio-3(2H)-pyridazin-3-one derivatives of the general formula I are suitable for effectively combating pests from the class of insects, mites and nematodes. The may be used as pesticides in crop protection, and in the hygiene, stores protection and veterinary sectors.

Example sof injurious insects from the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grndiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hiphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityo-*

*campa, Tortrix viridana, Tricoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postia, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anaopheles maculipennis, Ceratitis capitata, Chrysomya bezziana, Chrysomya hominivorax, Chrysomya macellari, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Lirimyza sativae, Liriomyza trifolii, Lucilia caprina, Lucilia cuprina, Lucilia sericata, Lycoria pectoralis, Mayetiola destructor, Musca domenstica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the Nemathelminthes class are root-knot nematodes, such as *Meloidogyne hapla, Meloidogyne incognita, Meloidogyne javanica, Zysten bildende Nematoden, z.B. Globodera rostochiensis, Heterodera avenae, Hetrodera glycinae, Heterodera schatii, Hetrodera triflolii,* and stem and leaf eelworms, such as *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Paratylenchus neglectus, Paratylenchus penetrans, Paratylenchus curvitatus,* and *Paratylenchus goodeyi.*

The active ingredients may be applied for instance as such, or in the form of formulations or application forms prepared therefrom, e.g., directly sprayable solutions, powders, suspensions, dispensions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil solvent may be homogenized in water by means of wetting or dispensing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90,% by weight of active ingredient.

Example of formulations are given below.

I. 5 parts by weight of compound no. 47 is intimately mixed with 95 parts by weight of particulate kaolin. A dust is obtained containing 5% by weight of the active ingredient.

II. 30 parts by weight of compound no. 25 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 57 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 47 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 108 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

The active ingredient concentrations in the finished formulations may vary over a wide range. Generally, they are from 0.0001 to 10, and preferably from 0.01 to 1,%. The active ingredients may also successfully be used in the ultra-low-volume (ULV) method, where it is possible to apply formulations containing more than 95wt. % of active ingredient, or even the active ingredient without additives.

In the open, the amount of active ingredient applied is for example from 0.001 to 10, particularly from 0.05 to 2, and preferably from 0.05 to 0.5, kg/ha.

There may be added to the active ingredients (if desired, immediately before use (tankmix) oils of various types, herbicides, fungicides, other pesticides and bactericides. These agents may be added to the active ingredients according to the invention in a weight ratio of from 1:10 to 10:1.

MANUFACTURING EXAMPLE 2-tert-Butyl-4-chloro-5-[(3-isopropylisoxazol-5-yl)-methylthio]-3(2H)-pyridazin-3-one (compound no. 8)

At room temperature (20° C.), 6.1 g (0.038 mol) of 5-chloromethyl-3-isopropylisoxazole is added to 8.3 g (0.038 mol) of 2-tert-butyl-4-chloro-5-mercapto-3-(2H)-pyridazinone and 5.2 g (0.038 mol) of potassium carbonate in 50 ml of dimethylformamide. The solution is stirred for 2 hours at 80° C. and overnight at room temperature, and then poured into 200 ml of water. After extraction with ethyl acetate, the organic phase is washed twice with water, dried over magnesium sulfate and concentrated, and the residue is recrystallized from a 4:1 mixture of an-hexane/ethyl acetate. There is obtained 8.5 g (66%) of 2-tert-butyl-4-chloro-5-[(3-isopropylisoxazol-5-yl)-methylthio]-3(2H)-pyridazin-3-one as colorless crystals; m.p.: 94°–96° C.

The compounds I listed in Tables 1 and 2 below may readily be obtained from corresponding atarting materials by the process according to the invention:

TABLE 1

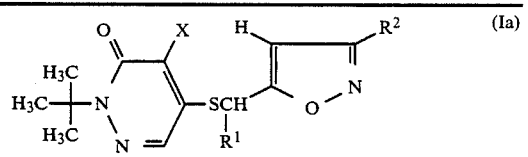

(Ia)

| Comp. No. | X | R$^1$ | R$^2$ | mp. [°C.] |
|---|---|---|---|---|
| 1 | Cl | H | CH$_3$ | 127–129 |
| 2 | Br | H | CH$_3$ | |
| 3 | Cl | CH$_3$ | CH$_3$ | |
| 4 | Cl | H | ethyl | 108–110 |
| 5 | Cl | CH$_3$ | ethyl | |
| 6 | Cl | H | n-propyl | 82–84 |
| 7 | Cl | CH$_3$ | n-propyl | |
| 8 | Cl | H | isopropyl | 94–96 |
| 9 | Cl | CH$_3$ | isopropyl | |
| 10 | Br | H | isopropyl | |
| 11 | Cl | H | n-butyl | 52–54 |
| 12 | Cl | CH$_3$ | n-butyl | |
| 13 | Br | H | n-butyl | |
| 14 | Cl | H | sec.-butyl | 58–60 |
| 15 | Cl | CH$_3$ | sec.-butyl | |
| 16 | Cl | H | tert.-butyl | 106–109 |
| 17 | Cl | CH$_3$ | tert.-butyl | |
| 18 | Br | H | tert.-butyl | |
| 19 | Cl | H | n-hexyl | |
| 20 | Cl | H | 1-ethylpent-1-yl | oil |
| 21 | Cl | H | 2,4,4-trimethylpent-1-yl | 59–60 |
| 22 | Cl | H | cyclopropyl | 126–127 |
| 23 | Br | H | cyclopropyl | |
| 24 | Cl | H | cyclopentyl | |
| 25 | Cl | H | cyclohexyl | 88–92 |
| 26 | Cl | CH$_3$ | cyclohexyl | |
| 27 | Br | H | cyclohexyl | |
| 28 | Cl | H | (2,2-dimethyl)-vinyl | |
| 29 | Br | H | (2,2-dimethyl)-vinyl | |
| 30 | Cl | H | (1,2-dibrom-2,2-dimethyl)-ethyl | |
| 31 | Cl | H | trifluoromethyl | |
| 32 | Br | H | trifluoromethyl | |
| 33 | Cl | CH$_3$ | trifluoromethyl | |
| 34 | Cl | H | methoxymethyl | |
| 35 | Cl | H | (1-methoxy)-ethyl | 82–84 |
| 36 | Cl | CH$_3$ | (1-methoxy)-ethyl | |
| 37 | Br | H | (1-methoxy)-ethyl | |
| 38 | Cl | H | (1-methoxy)-propyl | |
| 39 | Cl | H | (2-methoxy)-propyl | |
| 40 | Cl | H | methoxycarbonyl | |
| 41 | Cl | CH$_3$ | methoxycarbonyl | |
| 42 | Cl | H | ethoxycarbonyl | 73–74 |
| 43 | Br | H | ethoxycarbonyl | |
| 44 | Cl | H | benzyl | |
| 45 | Cl | H | phenethyl | |
| 46 | Cl | CH$_3$ | 2-(4-tert.-butylphenyl)-1-methylethyl | resin |
| 47 | Cl | H | phenyl | 108–111 |
| 48 | Cl | CH$_3$ | phenyl | 50–52 |
| 49 | Br | H | phenyl | |
| 50 | Br | CH$_3$ | phenyl | |
| 51 | Cl | H | (2-methyl)-phenyl | |
| 52 | Cl | H | (3-methyl)-phenyl | |
| 53 | Cl | H | (4-methyl)-phenyl | 150–154 |
| 54 | Cl | H | (2-ethyl)-phenyl | |
| 55 | Cl | H | (4-ethyl)-phenyl | |
| 56 | Cl | H | (4-isopropyl)-phenyl | |
| 57 | Cl | H | (4-tert.-butyl)-phenyl | 127–128 |
| 58 | Cl | H | (2,4-dimethyl)-phenyl | |
| 59 | Cl | H | (3,5-di-tert.-butyl)-phenyl | |
| 60 | Cl | H | (2,4,6-trimethyl)-phenyl | |
| 61 | Cl | H | (4-phenyl)-phenyl | 136–140 |
| 62 | Cl | CH$_3$ | (4-phenyl)-phenyl | |
| 63 | Cl | H | (2-methoxy)-phenyl | |
| 64 | Cl | CH$_3$ | (2-methoxy)-phenyl | |

TABLE 1-continued

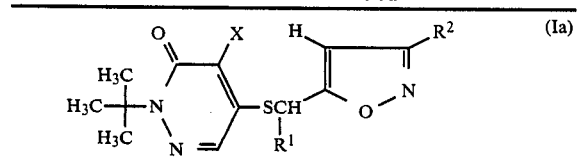

(Ia)

| Comp. No. | X | R¹ | R² | mp. [°C.] |
|---|---|---|---|---|
| 65 | Cl | H | (3-methoxy)-phenyl | |
| 66 | Cl | H | (4-methoxy)-phenyl | 148–150 |
| 67 | Cl | CH₃ | (4-methoxy)-phenyl | |
| 68 | Cl | H | (2-ethoxy)-phenyl | |
| 69 | Cl | H | (3-ethoxy)-phenyl | |
| 70 | Cl | H | (4-ethoxy)-phenyl | |
| 71 | Cl | CH₃ | (4-ethoxy)-phenyl | |
| 72 | Cl | H | (4-tert.-butoxy)-phenyl | |
| 73 | Cl | H | (2-n-butoxy)-phenyl | 87–88 |
| 74 | Cl | H | (4-n-hexoxy)-phenyl | 70–78 |
| 75 | Cl | H | (2-n-octoxy)-phenyl | 70–71 |
| 76 | Cl | CH₃ | (2-n-octoxy)-phenyl | |
| 77 | Cl | H | (2,4-dimethoxy)-phenyl | |
| 78 | Cl | H | (3,5-dimethoxy)-phenyl | |
| 79 | Cl | H | (2,5-dimethoxy)-phenyl | |
| 80 | Cl | H | (2,3-dimethoxy)-phenyl | |
| 81 | Cl | H | (2,4,6-trimethoxy)-phenyl | |
| 82 | Cl | H | (2,3,4-trimethoxy)-phenyl | |
| 83 | Cl | H | (2,4,5-trimethoxy)-phenyl | |
| 84 | Cl | H | (4-trifluoromethyl)-phenyl | 157–160 |
| 85 | Cl | CH₃ | (4-trifluoromethyl)-phenyl | |
| 86 | Cl | H | (2-trifluoromethyl)-phenyl | resin |
| 87 | Cl | H | (3-trifluoromethyl)-phenyl | |
| 88 | Cl | H | (chlorodifluoromethyl)-phenyl | |
| 89 | Cl | H | (4-difluoromethoxy)-phenyl | |
| 90 | Cl | H | 2-(1,1,2,2-tetrafluoroethoxy)-phenyl | resin |
| 91 | Cl | H | 3-(1,1,2,2-tetrafluoroethoxy)-phenyl | |
| 92 | Cl | H | 4-(1,1,2,2-tetrafluoroethoxy)-phenyl | |
| 93 | Cl | H | (2-fluoro)-phenyl | resin |
| 94 | Cl | CH₃ | (2-fluoro)-phenyl | |
| 95 | Cl | H | (3-fluoro)-phenyl | 128–134 |
| 96 | Br | H | (3-fluoro)-phenyl | |
| 97 | Cl | H | (4-fluoro)-phenyl | 165–167 |
| 98 | Cl | CH₃ | (4-fluoro)-phenyl | |
| 99 | Cl | H | (2-chloro)-phenyl | resin |
| 100 | Cl | CH₃ | (2-chloro)-phenyl | |
| 101 | Cl | H | (3-chloro)-phenyl | |
| 102 | Cl | H | (4-chloro)-phenyl | 166–170 |
| 103 | Cl | H | (3-bromo)-phenyl | |
| 104 | Cl | H | (3-bromo)-phenyl | |
| 105 | Cl | H | (4-bromo)-phenyl | |
| 106 | Cl | H | (2,6-difluoro)-phenyl | resin |
| 107 | Cl | CH₃ | (2,6-difluoro)-phenyl | |
| 108 | Cl | H | (2-chloro-6-fluoro)-phenyl | 125–128 |
| 109 | Cl | CH₃ | (2-chloro-6-fluoro)-phenyl | |
| 110 | Br | H | (2-chloro-6-fluoro)-phenyl | |
| 111 | Cl | H | (2,3-dichloro)-phenyl | |
| 112 | Cl | H | (3,4-dichloro)-phenyl | 133–135 |
| 113 | Cl | CH₃ | (3,4-dichloro)-phenyl | |
| 114 | Cl | H | (2,4-dichloro)-phenyl | |
| 115 | Cl | H | (3,5-dichloro)-phenyl | |
| 116 | Cl | H | (2,3,4-trichloro)-phenyl | |
| 117 | Cl | H | (2-chloro-6-nitro)-phenyl | |
| 118 | Cl | H | (4-chloro-3-nitro)-phenyl | |
| 119 | Cl | H | (2-chloro-5-nitro)-phenyl | |
| 120 | Cl | H | (5-chloro-2-nitro)-phenyl | |
| 121 | Cl | H | (2,4-dichloro-5-nitro)-phenyl | |
| 122 | Cl | H | (2,6-dichloro-3-nitro)-phenyl | |
| 123 | Cl | H | (3-bromo-4-methoxy)-phenyl | 147–149 |
| 124 | Cl | CH₃ | (3-bromo-4-methoxy)-phenyl | |
| 125 | Cl | H | (5-bromo-2-methoxy)-phenyl | |
| 126 | Cl | H | (2-nitro)-phenyl | |
| 127 | Br | H | (2-nitro)-phenyl | |
| 128 | Cl | H | (3-nitro)-phenyl | 127–129 |
| 129 | Cl | CH₃ | (3-nitro)-phenyl | |
| 130 | Br | H | (3-nitro)-phenyl | |
| 131 | Cl | H | (4-nitro)-phenyl | |
| 132 | Cl | H | (2,4-dinitro)-phenyl | |
| 133 | Cl | H | (4-methyl-3-nitro)-phenyl | |
| 134 | Cl | H | (4-phenoxy)-phenyl | 117–119 |
| 135 | Cl | CH₃ | (4-phenoxy)-phenyl | |
| 136 | Br | H | (4-phenoxy)-phenyl | |

TABLE 1-continued

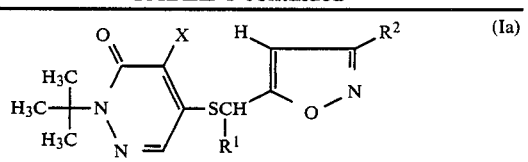

(Ia)

| Comp. No. | X | R¹ | R² | mp. [°C.] |
|---|---|---|---|---|
| 137 | Cl | H | (2-cyano)-phenyl | |
| 138 | Cl | CH₃ | (2-cyano)-phenyl | 164–169 |
| 139 | Cl | H | (4-cyano)-phenyl | |
| 140 | Cl | CH₃ | (4-cyano)-phenyl | |
| 141 | Br | H | (4-cyano)-phenyl | |

TABLE 2

(Ib)

| Comp. No. | X | R¹ | R² | R³ | mp. [°C.] |
|---|---|---|---|---|---|
| 142 | Cl | H | CH₃ | CH₃ | 137–140 |
| 143 | Cl | H | CH₃ | Br | |
| 144 | Cl | H | isopropyl | CH₃ | |
| 145 | Cl | H | isopropyl | Br | |
| 146 | Cl | H | phenyl | H | |
| 147 | Cl | H | phenyl | CH₃ | |
| 148 | Cl | H | phenyl | Br | |
| 149 | Cl | H | (2-fluoro)-phenyl | CH₃ | |
| 150 | Cl | H | (4-fluoro)-phenyl | CH₃ | |
| 151 | Cl | H | (2-chloro-6-fluoro)-phenyl | CH₃ | |

USE EXAMPLES

In the following examples, the action on pests of the compounds according to the invention, or agents containing them, was compared with that of the following prior art compound, or agents containing it:

A: [structure shown]

disclosed in EP-A-199 281 as compound no. 866

The concentrations at which the investigated compounds achieve a 100% kill or inhibitition are the minimum concentrations. At least one replicate was run for each concentration.

EXAMPLE A

Tetranychus telarius (spinning mite); contact action; spray experiment

Potted bush beans which had developed the first pair of true leaves and were under attack from all stages of the spinning mite Tetranychus telarius were sprayed to runoff in a spray cabinet with aqueous formulations of the active ingredients. The plants were placed on a turntable and sprayed from all sides with 50 ml of spray liquor. Spraying lasted for about 22 seconds. After 8 days the plants were investigated for living mites.

In this experiment, the lethal dose of compound no. 25 was 0.02wt. % and of compound no. 57 0.04wt. %. Compound no. 47 achieved 80% kill at a rate of 0.004wt. %. Comparative compound A had no effect (0% kill) at a rate of 0.1wt. %.

EXAMPLE 8

*Tetranychus telarius* (spinning mite); experiment with counted females

Potted bush beans were placed on a turntable in a spray cabinet and sprayed to runoff with aqueous formulations of the active ingredients. After drying, pieces 25 mm in diameter are stamped from the leaves. These pieces were placed on cellulose whose edges dipped continuously in water. Ten adult females were placed on each leaf piece. The kill rate was determined after 10 days.

In this experiment, compound no. 47 achieved an 80% kill at a rate of 0.002wt. %.

EXAMPLE C

Breeding experiment with *Dysdercus intermedius* (cotton stainer)

1 ml of acetonic solutions of the active ingredients were used to line Petri dishes 10 cm in diameter. After the solvent had evaporated, 20 larvae of the penultimate stage were placed in the dishes. After 24 hours the survivors were transferred to 1 liter jars containing 200 g of sterile quartz sand (particle size: 0 to 3 mm). This sand had been watered prior to the experiment with 25 ml of aqueous formulations of the active ingredients. The food proffered was swollen cotton seeds which were replaced once a week. The sand was also moistened once a week with pure water.

The temperature was kept at 25° to 27° C. The jars were monitored until the eggs in the controls hatched.

In this experiment, the kill rate of compound no. 47 was 4 ppm. Comparative compound A had no effect (0% kill) at a rate of 25 ppm.

EXAMPLE D

Ovicidal action on *Dysdercus intermedius* (cotton stainer)

Pieces of adhesive tap (about 0.8 cm) were stuck to the top edge of plastic plant markers. 24 hours before commencement of the experiment, eggs of the cotton stainer contained in a vessel were attached to the adhesive strips by dipping the markers into the vessel. The eggs were then dipped for 5 seconds into aqueous formulations of the active ingrtedients and excess liquid was allowed to drip off onto filter paper, care being taken to prevent the eggs coming into contact with the paper. The markers were then placed in plastic trays (adhesive strip at the top). Half a roll of absorbent cotton was moistened with water and placed in each beaker to prevent drying out, and the trays were covered with a glass plate. Assessment took place after the control bugs hatched (after about 8 days). Hatch inhibition was assessed in %.

In this experiment, compound no. 47 achieved 80% inhibition at a rate of 0.01wt. %, compound no. 108 gave 90% inhibition at 0.1wt. %, and comparative compound A had no effect (0% hatch inhibition) at 0.1wt. %.

EXAMPLE E

Action on eggs of *Plutella maculipennis* (diamondback moth)

Young cabbage plants having two to three pairs leaves bearing numerous diamondback moth eggs were sprayed to runoff with aqueous emulsions of the active ingredients. The plants were then kept under greenhouse conditions and the leaf area consumed by the hatched caterpillars was determined.

In this experiment, compound no. 47 achieved 85% eating inhibition at a rate of 0.002wt. %.

EXAMPLE F

Contact action on Epilachna varivestis (Mexican bean beetle)

Petri dishes 10 cm in diameter were lined with acetonic formulations of the active ingredients. After the solvent had evaporated, 5 larvae (3 to 4 mm) were placed in each dish. The kill rate was assessed after 24 hours.

In this experiment, compound no. 47 achieved 85% kill at a rate of 0.06 mg.

We claim:

1. A 2-tert-butyl-5-isoxazolylmethylthio-3(2H)-pyridazin-3-one compound of the formula I

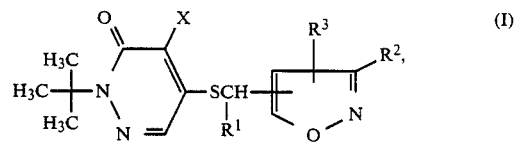

where $R^1$ is hydrogen or $C_1$–$C_4$-alkyl, $R^2$ is hydrogen, $C_1$–$C_8$-alkyl, $C_2$–$C_8$-alkenyl, $C_1$–$C_4$-haloalkyl, $C_2$–$C_8$-alkoxyalkyl, $C_3$–$C_{10}$-cycloalkyl, $C_2$–$C_5$-alkoxycarbonyl, phenyl, $C_7$–$C_{10}$-phenylalkyl, phenyl which is mono-, di- or trisubstituted by halogen, $C_1$–$C_8$-alkyl, $C_1$–$C_8$-alkoxy, $C_1$–$C_4$-haloalkyl, $C_1$–$C_4$-haloalkoxy, phenyl, phenoxy or cyano, and/or mono- or disubstituted by nitro, or is $C_7$–$C_{10}$-phenylalkyl substituted in the phenyl moiety, $R^3$ is hydrogen, halogen, $C_1$–$C_8$-alkyl or $C_2$–$C_8$-alkenyl, and X is chlorine or bromine.

2. A pesticide containing a pesticidally effective amount of a 2-tert-butyl-5-isoxazolylmethylthio-3(2H)-pyridazin-3-one derivative as set forth in claim 1 and conventional carriers therefor.

3. A pesticide as set forth in claim 2, containing from 0.1 to 95wt. % of a 2-tert-butyl-5-isoxazolylmethylthio-3(2H)-pyridazin-3-one derivative of the formula I.

4. A process for combating, insects, mites and methods wherein such pests or the areas or rooms to be kept free from such pests are treated with a pesticidally effective amount of a 2-tert-butyl-5-isoxazolylmethylthio-3(2H)-pyridazin-3-one derivative of the formula I as set forth in claim 1.

5. A 2-tert-butyl-5-isoxazolylmethylthio-3(2H)-pyridazin-3-one compound of the formula Ia

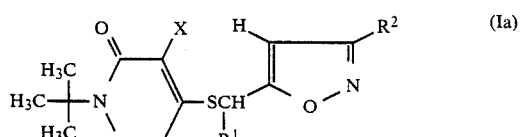

where $R^1$ is hydrogen or $C_1$–$C_4$-alkyl, $R^2$ is hydrogen, $C_1$–$C_8$-alkyl, $C_2$–$C_8$-alkenyl, $C_1$–$C_4$-haloalkyl, $C_2$–$C_8$-alkoxyalkyl, $C_3$–$C_{10}$-cycloalkyl, $C_2$–$C_5$-alkoxycarbonyl, phenyl, $C_7$–$C_{10}$-phenylalkyl, phenyl which is mono-, di- or trisubstituted by halogen, $C_1$–$C_8$-alkyl, $C_1$–$C_8$-alkoxy, $C_1$–$C_4$-haloalkyl, $C_1$–$C_4$-haloalkoxy, phenyl, phenoxy or cyano, and/or mono- or disubstituted by nitro, or is $C_7$–$C_{10}$-phenylalkyl substituted in the phenyl moiety, and X is chlorine or bromine.

* * * * *

UNITED STATES PATENT AND TRADEMARK OFFICE
CERTIFICATE OF CORRECTION

PATENT NO. : 4,929,617

DATED : May 29, 1990

INVENTOR(S) : Joachim LEYENDECKER, et al

It is certified that error appears in the above-identified patent and that said Letters Patent is hereby corrected as shown below:

On the title page:

The title is incomplete, it should read as follows

--2-TERT-BUTYL-5-ISOXAZOLYLMETHYLTHIO-3(2H)-PYRIDAZIN-3-ONE DERIVATIVES--

Signed and Sealed this

Third Day of September, 1991

Attest:

HARRY F. MANBECK, JR.

Attesting Officer

Commissioner of Patents and Trademarks